United States Patent [19]
Xia et al.

[11] Patent Number: 6,139,533
[45] Date of Patent: Oct. 31, 2000

[54] HYPODERMIC NEEDLE CAPPING DEVICE

[76] Inventors: Frank Zhishi Xia; Gunther Maier; Jack Yongfeng Zhang; Mary Ziping Luo, all of 1886 Santa Anita Ave., El Monte, Calif. 91733

[21] Appl. No.: 09/487,185

[22] Filed: Jan. 19, 2000

[51] Int. Cl.[7] .................................................... A61M 5/32
[52] U.S. Cl. ........................................... 604/192; 604/263
[58] Field of Search .................................... 604/192, 263, 604/110, 187; 128/919

[56]   References Cited

U.S. PATENT DOCUMENTS

| | | | |
|---|---|---|---|
| 5,116,325 | 5/1992 | Paterson | 604/192 |
| 5,207,653 | 5/1993 | Janjua et al. | 604/263 X |
| 5,462,534 | 10/1995 | Debreczeni | 604/192 |
| 5,913,846 | 6/1999 | Szabo | 604/263 |

*Primary Examiner*—John D. Yasko
*Attorney, Agent, or Firm*—Albert O. Cota

[57]   ABSTRACT

A hypodermic needle capping device (10) that attaches to a hypodermic syringe (100). The device (10) consists of two separate elements: the first consists of a collar (12) having integrally attached a snap-lock structure (24) that includes a locking barb (40) and slide member retaining structure (42). The second consists of a slide member (54) which includes a barb receiving and locking slot (58) and a needle point barrier (76). The collar (12) is frictionally inserted over the upper edge (108) of the syringe (100). The slide member (54) is slidably attached to the slide member retaining structure (42) and is designed to be placed in two positions. When the syringe (100) is to be used, the slide member (54) is positioned along the side of the syringe (100). After the syringe has been used, but prior to being discarded, the slide member (54) is single-handedly slid upward until the locking barb (40) is inserted into the slot (58) at which time the slide member (54) is positioned with the syringe needle (104) point adjacent the needle point barrier (76).

16 Claims, 2 Drawing Sheets

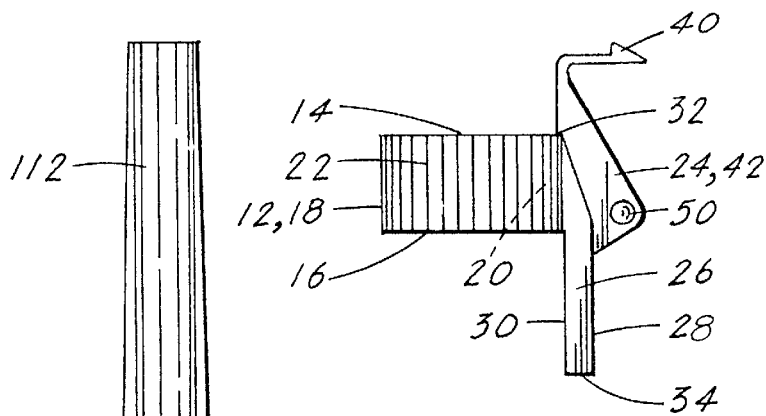
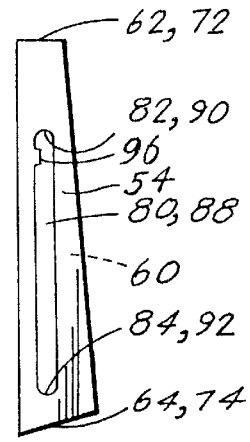
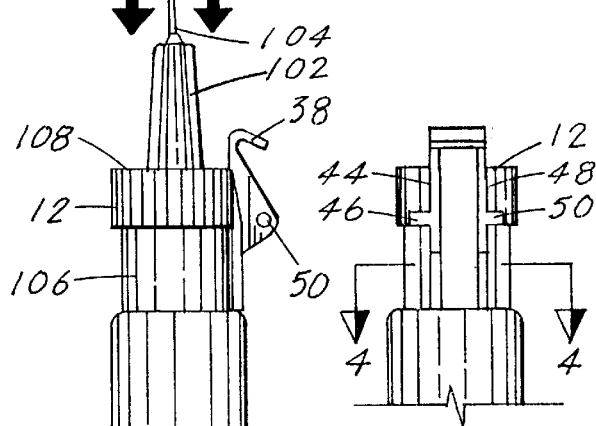
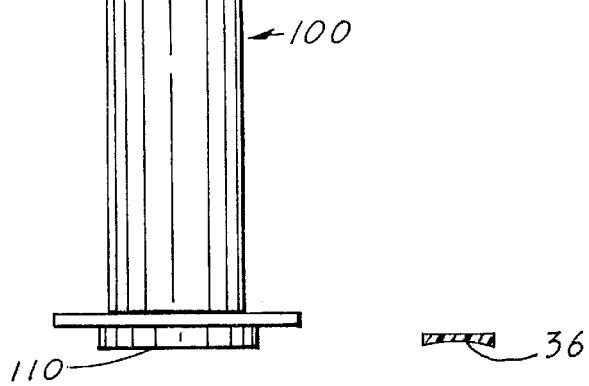
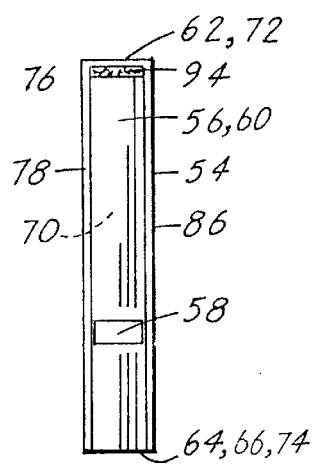

HYPODERMIC NEEDLE CAPPING DEVICE

TECHNICAL FIELD

The invention pertains to the general field of hypodermic syringes and more particularly to a hypodermic needle capping device that allows the needle of the syringe to be single-handedly capped after use.

BACKGROUND ART

Health-care professionals, such as doctors, nurses and blood technicians face a wide variety of potentially dangerous situations resulting from their chosen profession. One of the most serious, and most prevalent is the danger from being accidentally punctured from a hypodermic syringe. All of the health-care professionals listed above, as well as others, face this danger, due to the fact that they all, at one time or another, have to use a hypodermic syringe on a patient.

The danger is not so much seen in the damage caused to a person's skin when they are punctured, but rather what is potentially being transferred into their bodies via their bloodstream from a syringe that has been previously used on a patient suffering from some sort of infection. Of course, there are some infections that pose little or no risk, but there are others, such as a serious blood infection and even HIV/AIDS, which is commonly known to imminently cause death.

For a long time, many hypodermic syringe companies tried to downplay the dangers of working with syringes. While it is true that many more people are punctured who do not become infected than there are those who do become infected; when you are dealing with a disease such as AIDS, where there is no cure and death is imminent, even one infection as a result of accidental puncturing is too many.

Some hypodermic syringe companies have attempted to solve this problem by creating syringes with shields or other safety devices. Unfortunately, in addition to often being clumsy and difficult to work with, these shields are frequently ineffective in actually preventing accidental punctures. If there were some design available that could provide true protection against accidental puncturing, while not altering the look and/or feel of a typical syringe, it would be a great benefit for many people.

A search of the prior art did not disclose any patents that read directly on the claims of the instant invention however, the following U.S. patents are considered related:

| U.S. PAT. NO. | INVENTOR | ISSUED |
| --- | --- | --- |
| 5,947,933 | Reichenbach | 7 September 1999 |
| 5,899,883 | Chern | 3 May 1999 |
| 5,713,871 | Stock | 3 February 1998 |
| 5,348,544 | Sweeney | 20 September 1994 |
| 4,834,716 | Ogle II | 30 May 1989 |

The U.S. Pat. No. 5,947,933 discloses a hypodermic syringe assembly provided with a syringe barrel and a safety shield telescoped over the syringe barrel and movable from a proximal position to a distal position. The safety shield is irreversibly lockable in the distal position on the syringe barrel to protectively shield a used needle cannula. The safety shield is releasably retained in a proximal position by engagement of a protrusion on the barrel and a groove on the shield. Engagement between the protrusion and the stop block can be overcome by rotating the safety shield. The safety shield may then be moved into an irreversible shielding position surrounding the needle cannula. The releasable retention of the safety shield in its proximal position prevents inadvertent distal movement of the safety shield.

The U.S. Pat. No. 5,899,883 patent discloses a safety syringe includes a tubular barrel having a bottom formed with an opening and a top formed with a neck portion, a plunger configured to be slidably fitted in the barrel and provided with a rubber piston at an inner end thereof and a thumb plate at an outer end thereof. A cylindrical connector is also included having a bottom formed with a flange, a first annular projection above the flange, and a second annular projection above the first annular projection, and a needle including a tubular pin and a conical base at a lower end of the tubular pin.

The U.S. Pat. No. 5,713,871 discloses a hypodermic needle having a rigid, clear, protective sleeve encircling the perimeter of the barrel of the hypodermic needle. Connected to the plunger of the hypodermic needle is the protective sleeve which is drawn toward the bevel of the hypodermic needle as the plunger is depressed. Additionally, the hypodermic needle includes a locking device that locks the protective sleeve in place once the plunger is fully depressed and the injection is complete. Thus, preventing reuse of the hypodermic needle and reducing the chance of accidental contact with the bevel.

The U.S. Pat. No. 5,348,544 discloses a safety shield for a medical implement having a needle cannula. The safety shield includes a guard that is slidably movable along the needle cannula from a proximal position where the tip of the needle cannula is exposed to a distal position where the tip of the needle cannula is safety shielded. A hinged arm connects the guard to a hub of the needle cannula or to the medical implement with which the needle cannula is used. The hinged arm can be collapsed upon itself, such that the guard is adjacent the hub of the needle cannula. Alternatively, the hinged arm can be extended to cause the guard to move distally along the needle cannula and into a position for shielding the tip of the needle cannula.

The U.S. Pat. No. 4,834,716 discloses a protective device for enclosing the scarf of a cannula that is carried by a boss while permitting access to the scarf by a port of a Y-site which is located into proximity to an adjoining length of flexible tubing, thus forming part of an intravenous administration set. The protective device has a cylindrical sheath surrounding the cannula, and the ends of the cylindrical portion have at least one cutout which snugly receives the flexible tubing.

For background purposes and as indicative of the art to which the invention relates, reference may be made to the following remaining patents found in the search:

| U.S. PAT. NO. | INVENTOR | ISSUED |
| --- | --- | --- |
| 5,938,641 | Villanueva | 17 August 1999 |
| 5,891,092 | Castellano | 6 April 1999 |
| 5,885,256 | Chern | 23 March 1999 |
| 5,876,382 | Erickson | 2 March 1999 |

DISCLOSURE OF THE INVENTION

The hypodermic needle capping device is designed to be attached to and function in combination with a hypodermic syringe which includes a needle hub, a needle and a hollow barrel having an upper edge and a plunger receiving lower edge. The invention provides a means for single-handedly and easily capping the tip of the needle to prevent an accidental puncturing of the skin. The device is attached along the side of the syringe's hollow barrel and is only activated after the syringe has been used and before the syringe is discarded in a sharps container.

In its basic design, the hypodermic needle capping device consists of:

a) A collar having an outside diameter and an inside diameter. The inside diameter is press-fitted over the upper edge of the syringe's hollow barrel,
b) A snap-lock structure having a longitudinal member attached to the outside diameter of the collar. The structure includes:
   (1) An upper edge from where extends outward a resilient locking tab and,
   (2) An outer surface from where extends a slide-member retaining structure, and
c) A slide member having:
   (1) Means for being slidably attached to the slide-member retaining structure,
   (2) An upper needle-point barrier, and
   (3) A locking tab receiving and locking slot.

The collar can be designed to include a series of vertical serrations which aid in inserting the collar over the upper edge of the hollow barrel. The collar as well as the attached snap-lock structure and the slide-member are preferably injected molded of a plastic.

The locking tab which extends from the upper edge of the snap-lock structure can be designed with a straight tab or preferably configured as a locking barb. The barb shape assures a positive lock which prevents the sliding member from being removed once the sliding member is in its locked, needle safe position.

The means for slidably attaching the slide-member to the slide-member retaining structure is accomplished by designing the structure with a first side wherefrom extends outward a first guide pin and a second side wherefrom extends outward a second guide pin. The corresponding slide member includes a central longitudinal member which has a locking tab receiving and locking slot. The longitudinal member also has an inner channel which includes a needle point barrier, a first side having a first longitudinal pin traversing slot and a second side having a second longitudinal pin traversing slot. The slide member is dimensioned to be slidably attached when the first and second longitudinal pin traversing slots are inserted over the first and second guide pins respectively.

When the hypodermic syringe is being used, the slide member is positioned in a downward direction along the slide-member retaining structure; after the hypodermic syringe has been used, but prior to disposal, the slide member is slid upward along the slide-member retaining structure until the locking tab receiving slot engages the locking tab at which time, the tip of the needle is safely located adjacent the upper needle-point barrier, thus safely capping the exposed needle of the hypodermic syringe.

In view of the above disclosure it is the primary object of the invention to provide a hypodermic needle capping device that allows the needle to be single-handedly capped after use and before disposal.

In addition to the primary object of the invention it is also an object to provide a hypodermic needle capping device that:

eliminates or substantially reduces the possibility of a syringe user accidently puncturing his finger with the syringe needle, is sanitary, does not take an unreasonably amount of additional space, can be made in various dimensions to accommodate various sizes of hypodermic syringes, and is cost effective from both a manufacturing and consumer points of view.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is a side elevational view of a hypodermic syringe having a collar and a snap-lock structure attached to the syringe barrel. The figure also shows a needle tip protector partially inserted over the needle.

FIG. 2 is a side elevational view of a collar and snap lock structure removed from the hypodermic syringe.

FIG. 3 is a rear elevational view of the collar and snap lock structure.

FIG. 4 is a cross sectional view of the longitudinal member of the snap-lock structure having a radiused surface which corresponds with the radiused surface of the syringe's barrel. The view is taken along the lines 4—4 of FIG. 3.

FIG. 5 is a side elevational view of the slide member showing the location of the pin traversing slots.

FIG. 6 is a front elevational view of the slide member showing the location of the locking tab receiving and locking slot. The figure also shows an optional needle tip engaging pad.

BEST MODE FOR CARRYING OUT THE INVENTION

Figure 7:
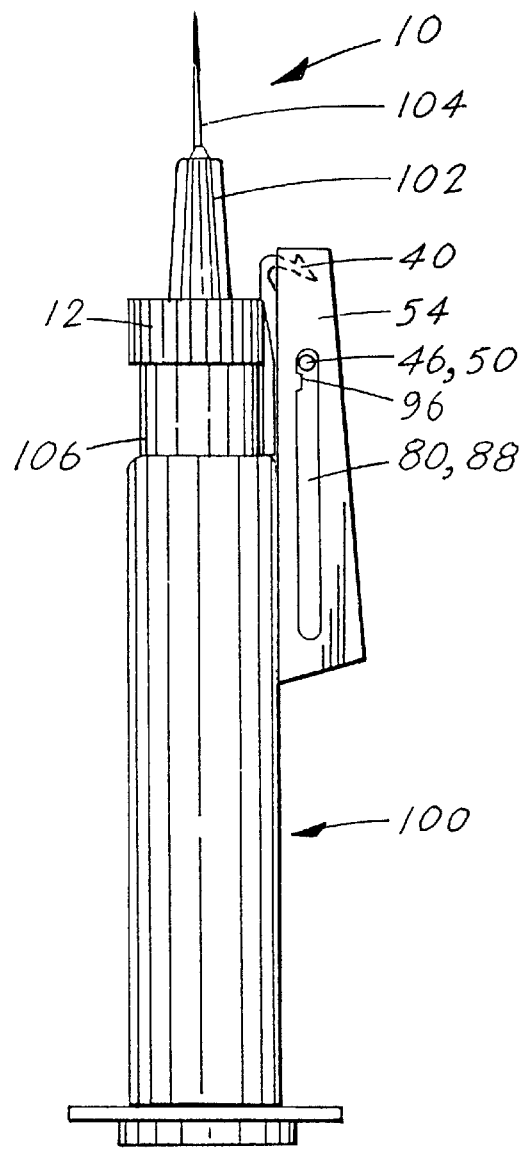
FIG. 7 is a side elevational view of the hypodermic needle capping device attached to a hypodermic syringe and shown positioned in the downward syringe usable position.

The best mode for carrying out the invention is presented in terms of a preferred embodiment for a hypodermic needle capping device 10, hereinafter "device 10". The device is designed to allow a health worker, such as a doctor, nurse, or blood technician to easily and safely use a hypodermic needle on a patient while significantly reducing the risk of accidently puncturing themselves, as well as the patient. With the risk of infectious diseases that are transferred via the bloodstream, and with HIV/AIDS is particular, a device such as this is not merely a benefit, but is also a potential lifesaver as well.

The device 10, as shown in FIGS. 1–8 is comprised of the following major elements: a collar 12, a snap-lock structure 24, a locking tab 38, a slide member retaining structure 42, a slide member 54, an outer channel 60, and an inner channel 70. In order to aide in the illustrative and descriptive process, a hypodermic syringe 100 having a needle hub 102, a needle 104, a hollow barrel 106 with an upper edge 108, a plunger receiving lower edge 110, and a cap 112 are also shown. It would be noted that the cap 112 is designed to fit over the needle hub 102 and to protect the needle 104 prior to use.

When the syringe 100 is about to be used, the cap 112 is removed, thus exposing the needle 104.

Figure 8:
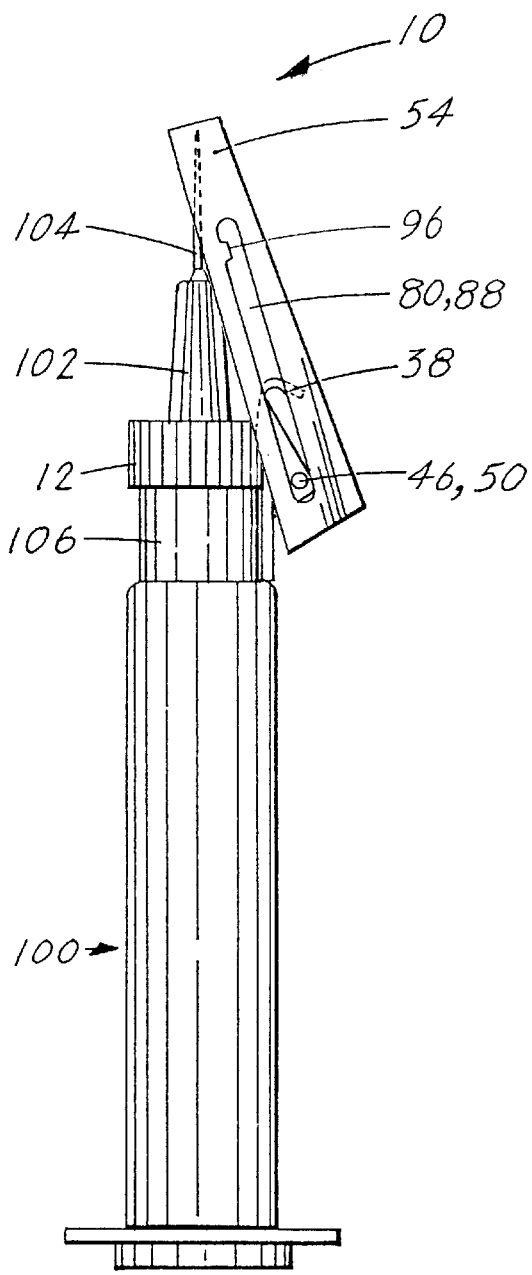
FIG. 8 is a side elevational view of the hypodermic needle capping device attached to a hypodermic syringe and shown positioned in an upward syringe non-usable position.

As shown in FIGS. 7 and 8, the device 10 functions in combination with the hypodermic syringe 100, and is comprised of the collar 12 which has an upper edge 14, a lower edge 16, an outside diameter 18, and an inside diameter 20 that is press-fitted over the upper edge 108 of the syringe's 100 hollow barrel 106. As shown in FIGS. 1, 2, 7 and 8, the outside diameter 18 of the collar 12 has a series of vertical serrations 22 which aid in sliding and positioning the collar 12 over the hollow barrier 106.

The snap-lock structure 24, as shown best in FIGS. 1, 2 and 3, is integrally molded with the collar 12 of a plastic and is comprised of a longitudinal member 26 having an outer surface 28, an inner surface 30, an upper edge 32 and a lower edge 34. The inner surface 30 is attached to the outside diameter 18 of the collar 12 as shown in FIG. 2. The locking tab 38 extends outward from the upper edge 32 and outer surface 28 of the longitudinal member 26, as shown in FIG. 1. The locking tab 38 can be designed as either a straight locking tab, or preferably as a locking barb 40, as shown in FIG. 2, which provides a positive lock upon the slide member 54 that prevents the slide member 54 from being removed once it has been placed in a needle safe position. The final element of the snap-lock structure 24 is the slide member retaining structure 42. The retaining structure 42, as shown in FIGS. 2 and 3, extends outward from the longitudinal member 26 and has a first side 44 from where extends outward a first guide pin 46. A second guide pin 50 extends outward from a second side 48, as shown in FIG. 3. Additionally, the inner surface 30 of the snap-lock structure 24 has a radiused surface 36, as shown in FIG. 4, that corresponds with the radiused surface of the hollow barrier 106.

In order to allow the hypodermic syringe's needle 104 to be safely covered, the slide member 54 is utilized. The slide member 54, as shown in FIGS. 5, 6, 7 and 8, is comprised of a central longitudinal member 56 having a locking barb receiving and locking slot 58; an outer channel 60 having an upper edge 62 and a lower edge 64, with the lower edge 64 having a closed surface 66; and an inner channel 70 having an upper edge 72 and a lower edge 74. As shown in FIGS. 5–8, the upper edge 72 includes a needle-point barrier 76, which extends across to the upper edge 62 of the outer channel 60. To the lower surface of the needle-point barrier 76 can be attached a needle tip engaging pad 94, which further provides a securing means for the needle 104. As also shown in FIG. 6 the slot 58 is located substantially one-third the distance from the lower edge 64 of the outer channel 60 of the slide member 54. In order to provide a high degree of structural integrity to the device 10, all of the elements of the slide member 54 are integrally molded of plastic.

The inner channel 70 further has a first side 78 having a first longitudinal pin traversing slot 80, which is comprised of an upper edge 82 and a lower edge 84 as shown in FIG. 5. A second side 86 has a second longitudinal pin traversing slot 88, which is also comprised of an upper edge 90 and a lower edge 92.

In order to move smoothly into position, the slide member 54 is dimensioned to be slidably attached when the first and second longitudinal pin traversing slots 80,88 are inserted over each of the first and second guide pins 46,50, respectively, as shown in FIGS. 7 and 8. The slide member 54 is designed to include a protuberance 96 that extends outward from an inner edge of the first and second pin traversing slots 80, 88, as shown in FIGS. 5, 7 and 8. The protuberances 96 are positioned whereby when the slide member 54 is in a downward position, the protuberances 96 are in contact with the lower surface of the first and second guide pins 46, 50 as shown in FIG. 7. The protuberances 96 function to maintain the slide member 54 in the downward position until such time that the user pushes the slide member 54 upward, overcoming the resistance of the protuberances 96 and allowing the slide member 54 to be placed in the upward position as shown in FIG. 8.

When the hypodermic syringe 100 is being used the slide member 54 is positioned in a downward direction with the respective upper edges 82,90 of the first and second pin traversing slots 80,88 as shown in FIG. 7. After the hypodermic syringe 100 has been used, but prior to disposal, the slide member 54 is slid upward until the locking tab 38 engages the receiving and locking slot 58. Once engaged, as shown in FIG. 8, the needle 102 is safely located adjacent the needle-point barrier 76 and presents no danger from an un-intentional puncturing.

While the invention has been described in complete detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

What is claimed is:

1. A hypodermic needle capping device that functions in combination with a hypodermic syringe comprising a needle hub, a needle and a hollow barrel having an upper edge and a plunger receiving lower edge, said device comprising:
    a) a collar having an outside diameter and an inside diameter, wherein the inside diameter is press-fitted over the upper edge of the hollow barrel,
    b) a snap-lock structure having a longitudinal member attached to the outside diameter of said collar, said structure having:
        (1) an upper edge from where extends outward a locking tab and,
        (2) an outer surface from where extends a slide-member retaining structure, and
    c) a slide member having:
        (1) means for being slidably attached to said slide-member retaining structure,
        (2) an upper needle-point barrier, and
        (3) a locking tab receiving and locking slot, wherein when the hypodermic syringe is being used, said slide member is positioned in a downward direction along said slide-member retaining structure; after the hypodermic syringe has been used, but prior to disposal, said slide member is slid upward along said slide-member retaining structure until the locking tab receiving slot engages the locking tab at which time, the tip of the needle is safely located adjacent the upper needle-point barrier, thus safely capping the exposed needle of the hypodermic syringe.

2. The device as specified in claim 1 wherein the longitudinal member of said snap-lock locking structure is integrally molded with said collar.

3. The device as specified in claim 1 wherein the locking tab is configured as a locking barb.

4. The device as specified in claim 3 wherein said means for slidably attaching said slide member to said slide-member retaining structure comprises:
    a) said slide member retaining structure having a first side wherefrom extends outward a first guide pin and a second side wherefrom extends outward a second guide pin, and b) said slide member having:
   (1) a central longitudinal member having a locking tab receiving and locking slot, and
   (2) an inner channel having a lower edge, an upper edge which includes a needle-point barrier, a first side having a first longitudinal pin traversing slot having an upper edge and a lower edge, and a second side having a second longitudinal pin traversing slot having an upper edge and a lower edge, wherein said slide member is dimensioned to be slidably attached when the first and second longitudinal pin traversing slots are inserted over the first and second guide pins respectively.

5. The device as specified in claim 1 wherein said slide member further comprises a protuberance that extends outward from an inner edge of said first and second pin traversing slots, wherein said protuberances are positioned whereby when said slide member is in a downward position, said protuberances are in contact with said first and second guide pins, wherein said protuberances maintain said slide member in the downward position until such time that a user pushes the slide member upward, overcoming the resistance of said protuberances and placing said slide member in the upward position.

6. The device as specified in claim 1 wherein said collar, said snap-lock structure and said slide member are all molded of plastic.

7. The device as specified in claim 1 wherein said collar having a series of vertical gripping serrations.

8. The device as specified in claim 1 wherein the hypodermic syringe further comprises a cap that fits over the needle hub, wherein the cap is removed and discarded prior to using the hypodermic syringe.

9. A hypodermic needle capping device that functions in combination with a hypodermic syringe comprising a needle hub, a needle and a hollow barrel having an upper edge and a plunger receiving lower edge, said device comprising:
   a) a collar having an upper edge, a lower edge, an outside diameter and an inside diameter that is press-fitted over the upper edge of the hollow barrel,
   b) a snap-lock structure comprising:
      (1) a longitudinal member having an outer surface, an inner surface, an upper edge and a lower edge, wherein the inner surface is integral to the outside diameter of said collar,
      (2) a locking barb extending outward from the upper edge and outer surface of said longitudinal member, and
      (3) a slide member retaining structure extending outward from the longitudinal member and having a first side wherefrom extends outward a first guide pin and a second side wherefrom extends outward a second guide pin,
   c) a slide member comprising:
      (1) a central longitudinal member having a locking barb receiving and locking slot,
      (2) an outer channel having an upper edge and a lower edge with the lower edge having a closed surface,
      (3) an inner channel having an upper edge and a lower edge, wherein the upper edge includes a needle-point barrier that extends across to the upper edge of the outer channel, with said inner channel further having a first side having a first longitudinal pin traversing slot having an upper edge and a lower edge, and a second side having a second longitudinal pin traversing slot having an upper edge and a lower edge,
      (4) a protuberance that extends outward from an inner edge of said first and second pin traversing slots, wherein said protuberances are positioned whereby when said slide member is in a downward position said protuberances are in contact with said first and second guide pins, wherein said protuberances maintain said slide member in a downward position, wherein said slide member is dimensioned to be slidably attached when the first and second longitudinal pin traversing slots are inserted over the first and second guide pins respectively, wherein when the hypodermic syringe is being used, said slide member is positioned in a downward direction with the respective upper edge of the first and second pin traversing slots, wherein after the hypodermic syringe has been used but prior to the syringe being disposed said slide member is slid upward, overcoming the resistance of said protuberances, until said locking tab engages said locking means receiving and locking barb at which time the needle point is safely located adjacent the needle-point barrier.

10. The device as specified in claim 9 wherein said locking barb receiving and locking slot is located substantially one-third the distance from the lower edge of the outer channel of the slide member.

11. The device as specified in claim 9 wherein the inner surface of the snap-lock structure has a radiused surface that corresponds with a radiused surface of said hollow barrel.

12. The device as specified in claim 9 wherein said snap-lock locking structure is integrally molded with said collar of a plastic.

13. The device as specified in claim 9 wherein all the elements of said slide member are integrally molded of a plastic.

14. The device as specified in claim 9 wherein the surface of the outside diameter of said collar having a series of vertical serrations to aid in sliding and positioning said collar over the hollow barrel of said hypodermic syringe.

15. The device as specified in claim 9 wherein said needle-point barrier has a lower surface to which is attached a needle tip engaging pad.

16. The device as specified in claim 9 wherein the hypodermic syringe further comprises a cap that fits over the needle hub, wherein the cap is removed and discarded prior to using the hypodermic syringe.

* * * * *